United States Patent [19]

Armstrong et al.

[11] 4,265,782

[45] May 5, 1981

[54] DETERGENT COMPOSITION

[75] Inventors: David P. Armstrong, Parsippany; Robert J. Verdicchio, Succasunna, both of N.J.

[73] Assignee: Johnson & Johnson Baby Products Company, New Brunswick, N.J.

[21] Appl. No.: 78,633

[22] Filed: Sep. 25, 1979

[51] Int. Cl.³ .................. C11D 10/02; C11D 1/94
[52] U.S. Cl. .................. 252/174.19; 252/DIG. 13; 252/174.16; 252/174.21; 252/174.22; 424/70
[58] Field of Search .................. 252/174.19, 174.21, 252/174.22, 174.16, DIG. 13; 424/70

[56] References Cited

U.S. PATENT DOCUMENTS

| 3,925,241 | 12/1975 | Schmolka | 252/DIG. 13 |
| 4,177,171 | 12/1979 | Walts | 252/DIG. 13 |
| 4,181,634 | 1/1980 | Kennedy et al. | 252/DIG. 13 |

*Primary Examiner*—Mayer Weinblatt
*Attorney, Agent, or Firm*—Steven P. Berman

[57] ABSTRACT

Improved detergent compositions are provided containing a modified rosin ester and at least one other surfactant selected from the group consisting of anionic, nonionic, cationic and amphoteric surfactants.

9 Claims, No Drawings

DETERGENT COMPOSITION

BACKGROUND OF THE INVENTION

The present invention relates to detergent compositions, and more particularly, to those detergent compositions which have relatively high viscosity and exhibit good cleansing properties and are mild and relatively nonirritating to the skin and eyes.

Nonirritating detergent compositions have been known in the art and have been in use for some time. U.S. Pat. Nos. 3,299,069 and 3,055,836 are representative of such prior art nonirritating detergent compositions.

These prior art compositions, although they are nonirritating and have good foaming characteristics, have very low viscosities. Increasing the viscosity of the compositions by employing viscosity building additives or thickeners results in a deterioration of the foaming and cleansing characteristics of the compositions and may result in other negative characteristics.

Increased viscosity without foam degeneration and with the maintenance of good cleansing characteristics is desirable in order to formulate detergent compositions, especially nonirritating shampoo compositions, that may be marketed as gel concentrates in tube-type containers. The tube-type formulations have found wide acceptance with consumers because of the inherent ease and control of the application of such high viscosity formulations to the hair. However, no satisfactory tube formulations of nonirritating type shampoos currently exist in the marketplace.

It is thus an object of the present invention to prepare detergent compositions which are effective for personal cleansing of the hair.

It is another object of the present invention to provide detergent compositions which provide good foam volume and foam stability.

It is still another object of the present invention to provide detergent compositions which while being effective cleansing agents exhibit low ocular irritancy.

It is a further object to provide detergent compositions which can be marketed as gel concentrates.

These and other objects of the present invention will become apparent to one skilled in the art from the detailed description given hereinafter.

SUMMARY OF THE INVENTION

This invention encompasses detergent compositions comprising as an active surfactant ingredient, a modified rosin ester, and at least one other surfactant selected from the group consisting of anionic, nonionic, cationic and amphoteric detergents. The balance of the compositions can comprise various detergency and cleansing adjuncts, fillers, carriers and the like which are well known in the art. The composition should have a pH in the range of about 7.2 to 8.1.

DETAILED DESCRIPTION OF THE INVENTION

The detergent compositions of the present invention comprise as active ingredients a modified rosin ester and at least one other surfactant. The modified rosin ester which are useful in the present invention are novel compounds described and claimed in copending patent application Ser. No. 78,634, filed Sept. 25, 1979.

These compounds are of the formula:

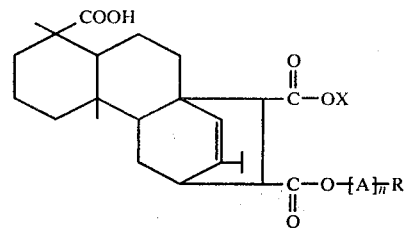

wherein R is hydrogen, alkyl containing from about 8 to 22 carbon atoms, hydroxyalkyl containing from about 8 1 to 22 carbon atoms, sorbitan monoesters of fatty acids containing from about 8 to 22 carbon atoms or alkyl phenoxy containing from about 8 to 22 carbon atoms; X is hydrogen or an alkali metal salt such as Na, K, Mg or Ca; A is $CH_2-CH_2-O$ or

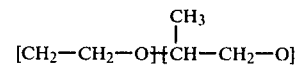

and n is an integer of at least 4 and preferably about 4 to 5000.

The modified rosin esters described above and useful in the present invention can be prepared in accordance with the process described in copending application Ser. No. 78,634 filed Sept. 25, 1979, the teachings of which are incorporated herein by reference.

Representative modified rosin esters useful in the present invention include compounds having the following structures:

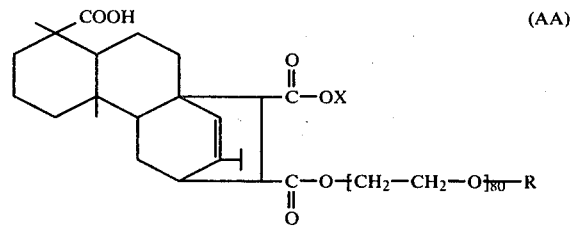

wherein R is sorbitan monopalmitate

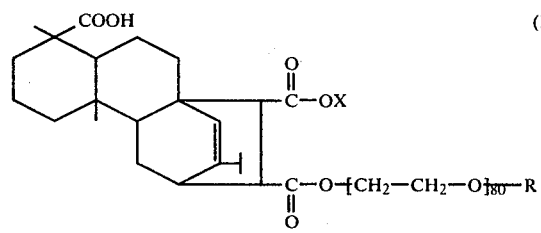

wherein R is sorbitan monolaurate

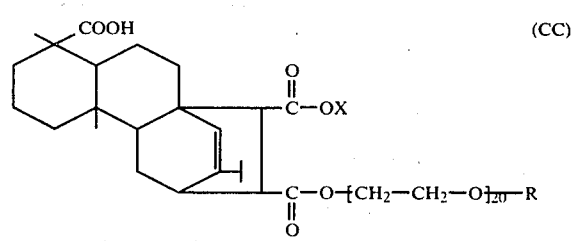

wherein R is sorbitan monococoate

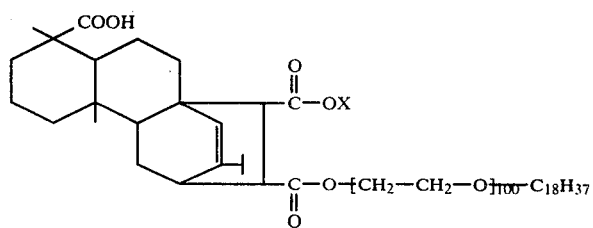
(DD)
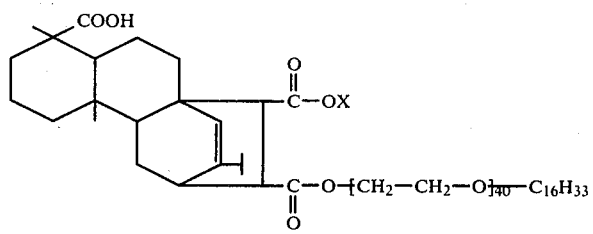
(EE)
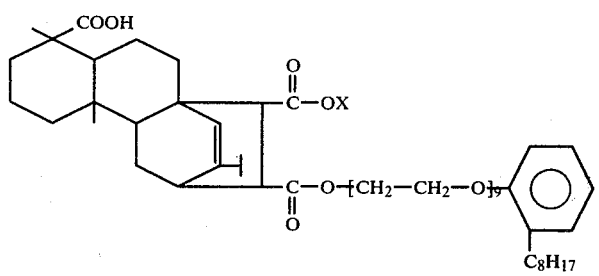
(FF)
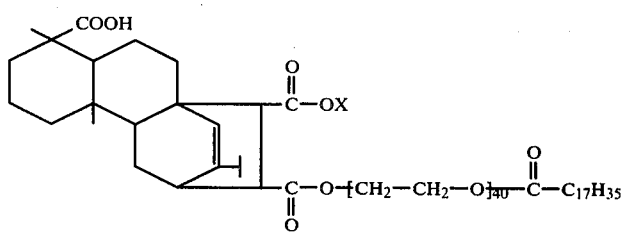
(GG)
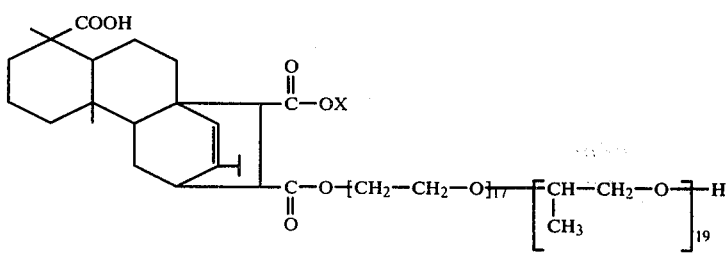
(HH)
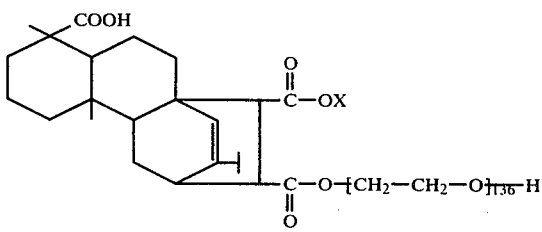
(II)
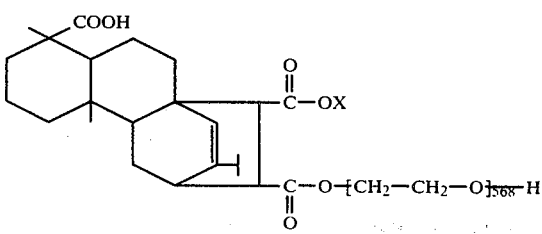
(JJ)

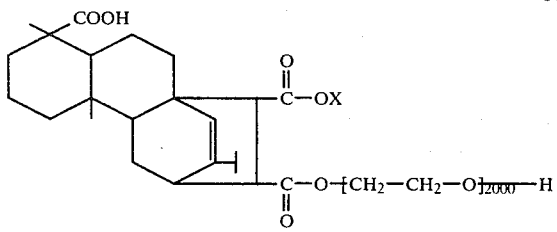
(KK)

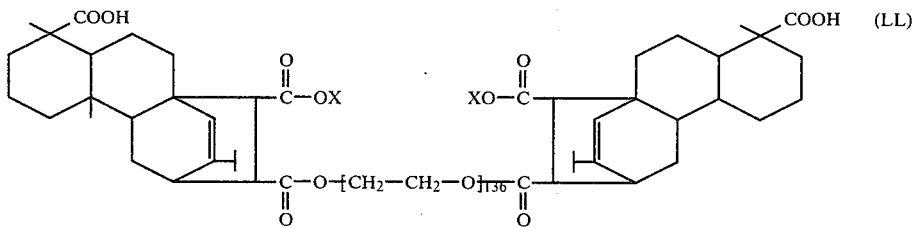
(LL)

The modified rosin esters can be utilized in the detergent compositions of the present invention in a range of from about 1 to 30% by weight of the total composition. These compounds when used in detergent compositions exhibit the desirable cleansing properties and easy "spreadability" and processing characteristics of anionic surfactants while unexpectedly also exhibiting the mildness characteristics of nonionic surfactants. Such is unexpected because rosinated materials are normally irritating to the eyes and skin. The excellent "spreadability" of compositions containing these compounds permits the formulation of excellent gel-type formulations of high viscosities while still retaining the good foaming and cleansing characteristics as well as the desired mildness characteristics.

As previously stated, the present invention relates to detergent compositions containing a modified rosin ester compound and at least one other surfactant selected from the group consisting of amphoteric, nonionic, anionic and cationic detergents. The amphoteric surfactants which may be used in the present invention include betaines, sultaines, phosphobetaines, phosphitaines, n-alkylamino propionates, n-alkylimino dipropionates and imidazolines.

The betaine and sultaine surfactants useful in this invention are described in U.S. Pat. No. 3,950,417 issued Apr. 13, 1976, which is incorporated herein by reference. The phosphobetaines and phosphitaines useful in this invention are described in copending applications Ser. Nos. 965,461 and 965,462 both filed Nov. 30, 1978, which are incorporated herein by reference. The n-alkylamino propionates and n-alkylimino dipropionates are sold under the tradename Deriphats by General Mills. The imidazolines which are useful in the compositions of this invention are described in U.S. Pat. No. 2,970,160.

The preferred betaine amphoteric surfactants include the alkylbetaines such as cocodimethylcarboxymethylbetaine, lauryldimethylcarboxymethylbetaine, lauryldimethylcarboxyethylbetaine, cetyldimethylcarboxymethylbetaine, lauryl-bis-(2-hydroxyethyl) carboxymethylbetaine, oleyldimethyl-gamma-carboxypropylbetaine, lauryl-bis-(2-hydroxypropyl)-carboxyethylbetaine, and the like; the sultaines such as cocodimethylpropylsultaine, stearyldimethylpropylsultaine, lauryl-bis-(2-hydroxyethyl) propylsultaine and the like; and the amidosultaines such as cocoamidodimethylpropylsultaine, stearylamidodimethylpropylsultaine, laurylamido-bis-(2-hydroxyethyl) propylsultaine, and the like.

The preferred phosphobetaines include lauric myristic amido 3-hydroxypropyl phosphobetaine, cocamido disodium 3-hydroxypropyl phosphobetaine, lauric myristic amido disodium 3-hydroxypropyl phosphobetaine, lauric myristic amido glyceryl phosphobetaine, lauric myristic amido carboxy disodium 3-hydroxypropyl phosphobetaine, and the like. The preferred phosphitaines include cocoamido propyl monosodium phosphitaine, lauric myristic amido propyl monosodium phosphitaine and the like.

The preferred n-alkylamino propionates and n-alkylimino dipropionates include those of the following structures:

$$R-\overset{\oplus}{N}H_2-CH_2-CH_2-COO^{\ominus}$$

and

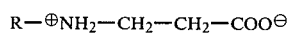
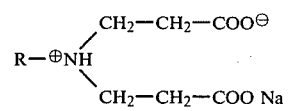

wherein R is from about 8 to 22 carbon atoms and mixtures thereof.

The amphoteric detergents may be present in an amount from about 2 to 10% by weight of the total composition.

It is envisioned that any anionic surfactant may be used in the compositions of the invention such as, for example, an alkyl sulfate of the formula $R-CH_2-OSO_3X$, an alkylether sulfate of the formula $R(OCH_2CH_2)_p-OSO_3X$, an alkylmonoglyceryl ether sulfonate of the formula $$R-OCH_2-\underset{\underset{OH}{|}}{CH}-CH_2-SO_3X,$$

an alkylmonoglyceride sulfate of the formula $$RCOOCH_2-\underset{\underset{OH}{|}}{CH}-CH_2OSO_3X,$$

an alkylmonoglyceride sulfonate of the formula

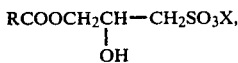

an alkyl sulfonate of the
formula RSO₃X, an alkylaryl sulfonate of the formula

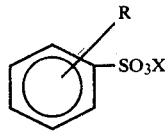

an alkyl sulfosuccinate of the formula

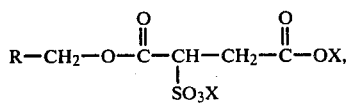

an alkyl sarcosinate of the formula

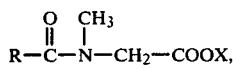

an acyl isethionate of the formula

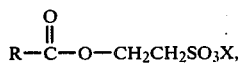

an alkyl methyl tauride of the formula

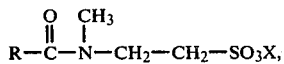

a fatty acid protein condensate of the formula

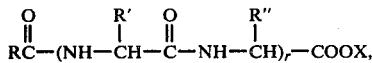

an alcohol ether carbosylate of the formula RO(CH₂CH₂O)$_q$—CH₂CO₂X and the like; wherein R is higheralkyl having from 7 to 17 carbon atoms; R' and R" are members each selected from the group consisting of hydrogen, loweralkyl, hydroxyloweralkyl, thioloweralkyl, carboxyloweralkyl, aminoloweralkyl, benzyl, and p-hydroxybenzyl; X is a member selected from the group consisting of alkali metal ions, alkaline earth metal ions, ammonium ions, and ammonium ions substituted with from 1 to 3 loweralkyls; p is an integer from about 1 to about 6; q is an integer from 2 to 6 and r is an integer from 2 to 10.

The preferred type of anionic surfactant is an alkyl ether sulfate, more preferably sodium tridecylalcohol ether sulfate in which p is 1 to 5. The anionic detergent may be present in an amount of from about 2 to 10% by weight of the total composition.

Nonionic detergents which are useful include the alkylene oxide ethers of phenols, fatty alcohols, and alkyl mercaptans; the alkylene oxide esters of fatty acid amides; the condensation products of ethylene oxide with partial fatty acid esters, and mixtures thereof. The polyoxyalkylene chain in such agents may contain from 5 to 100 alkylene oxide units in which each alkylene unit has from 2 to 3 carbon atoms.

The preferred nonionic surfactant in the compositions of the invention is a water-soluble polyoxyethylene derivative of a hydrophobic base, said derivative being a member of the group consisting of the reaction products of 9-20 carbon atom fatty acid monoesters of aliphatic polyhydric alcohols, which polyhydric alcohols contain at least 3 hydroxyls, with at least 10 moles of ethylene oxide, and preferably with from about 10 to about 100 moles of ethylene oxide.

The nonionic surfactant may be present in an amount of from about 1 to 30% by weight of the total composition.

Cationic surfactants suitable in these compositions include mono- and bis-quaternary ammonium halides, such as stearyldimethylbenzylammonium chloride, cetyltrimethylammonium chloride, N,N-dioctadecyl-N,N,N',N'-tetramethyl-1,5 (3 oxapentylene)diammonium bromide; tertiary amine salts such as cocamidopropyldimethylamine hydrochloride stearylamidopropyldimethylamine citrate; cationic polymers such as hydroxyethyl cellulose reacted with epichlorohydrin and then quaternized with trimethylamine. (Polymers of this type are sold by Union Carbide under the tradename Polymer JR.) and specific triesters of phosphoric acid. The specific triesters of phosphoric acid are described in copending patent application Ser. No. 078,634 filed Sept. 25, 1979, which is incorporated herein by reference. The cationic surfactants should be present in an amount of from about 0.5 to 3.0% by weight of the total composition.

The total amount of the active surfactant ingredients in the present invention should not be greater than about 40% by weight of the total composition in order to avoid ocular irritation problems, preferably from about 15 to 30% by weight of the total composition with the proviso that the total amount of anionic surfactant and amphoteric surfactant should not exceed 20% by weight of the total composition. In addition, other ingredients conventionally added to surfactant compositions for personal use, such as dyes, preservatives, perfumes, thickeners, opacifiers, conditioners, emollients, buffering agents, and the like, may be added in minor amounts. Ingredients such as dyes, preservatives and perfumes together usually constitute less than 2% by weight of the total composition and thickeners may be added to the composition in an amount of from about 1 to about 3% by weight of the total composition.

The detergent compositions of the present invention should have a pH in the range of about 7.2 to 8.1. At a pH of less than about 7.2, freeze-thaw problems may occur and at a pH of greater than about 8.1, difficulties in the spreadability characteristics of the compositions may begin to be noticed.

The detergent compositions of the present invention can be prepared by admixing the modified rosin ester with the other surfactant(s) at room temperature or slightly elevated temperatures (about 50° C.) and then sufficient deionized water is added to bring the composition to about three quarters of its intended weight. Other ingredients such as various detergency adjuncts, fillers, carriers, perfumes, preservatives and the like are added followed by the balance of the water. The pH is then adjusted within the range of about 7.2 to 8.1 by the addition of strong acid, e.g., HCl, or strong base NaOH, as needed.

The detergent compositions of the present invention can be tested for ocular irritation by the following modified Draize Test (J. H. Draize et al., Toilet Goods Assn. No. 17, May 1952, No. 1, Proc. Sci. Sect.).

An 0.1 ml. sample of a neutral composition under test is dropped into one eye of an albino rabbit, the other eye serving as a control. Six rabbits are employed for each composition. Observations are made after 1, 24, 48, 72 and 96 hours and 7 days after initial instillation; second and third instillations are made after the 24 and 48 hour readings. Results may vary from substantially no change or only a slight irritation in the appearance of the rabbit's eye after 7 days to severe irritation and/or complete corneal opacity. Ocular lesions are scored for the cornea, iris and conjunctiva with a higher number indicating greater ocular irritation and the scores are added to give a total numerical value for each reading for six rabbits and averaged. The averaged score is an indication of the irritation potential of the composition under test. Based on the averaged score, descriptive irritation evaluation may be given, e.g., none, slight, moderate, severe, as the case may be.

The detergent compositions of the invention provide high foam volume and moreover outstanding foam stability as measured by an adaption of the well-known Ross-Miles foam test principle ["Oil and Soap" 18.99-102 (1941)]:

Lanolin, anhydrous, cosmetic grade is mixed with dioxane (technical grade) in the proportion of 2.5 grams lanolin and 100 grams of dioxane. The lanolin is first mixed with 25 cc. of dioxane. This mixture is heated over a steam bath to 45° C. in order to dissolve the lanolin in the dioxane. The remainder of the dioxane is then added and mixed. This lanolin dioxane solution, which is stored in an amber bottle, should be prepared fresh on the day that the tests are run.

The composition to be tested is diluted by adding 376 cc. of distilled water to 4 grams of the composition, and then by adding 20 cc. of the lanolin-dioxane solution described above while mixing. Heat is produced when the lanolin-dioxane solution is added to the solution of the composition in water and care must be taken in adjusting the temperature of this solution to 24°–25° C. Both of these intermediate solutions should therefore be adjusted to 23° C. before mixing. The cooling of the lanolin-dioxane solution should be gradual in order to avoid precipitation of the lanolin. This will produce a final solution with a temperature of 24°–25° C.

The final solution of the composition to be tested, water, dioxane and lanolin described above, is then run in a modified Ross-Miles foam column in the usual way. All tests are conducted in duplicate, and the average of the two results is taken. Foam stability is determined by measuring the decay in foam height after two minutes, expressed as a percentage of the original height.

Specific embodiments of the detergent and cleansing compositions prepared in accordance with the present invention are illustrated by the following representative examples. It will be understood, however, that the invention is not confined to the specific limitations set forth in the individual examples, but rather to the scope of the appended claims.

EXAMPLE I

A gel-type composition is prepared by charging 104 grams of 45% active sultaine to a vessel equipped with a mechanical stirrer to which 155 grams of 32% active sodium tridecylether (4.2) sulfate and 182 grams of 24% active coconut imidazoline are added and the components are mixed. 207 grams of 70% active Compound AA are added and mixed unitl homogeneous followed by the addition of 0.0172 grams of dye and 200 grams of deionized water. The mixture is heated to 50° C. for about 20 minutes, then cooled to 35° C. and the pH is then adjusted to 7.3±0.1 with 10% HCl. 1.5 grams of preservative and 3.5 grams of fragrance are then added followed by the addition of sufficient deionized water to bring the total mass to 1000 grams resulting in a composition of the following ingredients:

| Ingredient | | % w/w |
|---|---|---|
| Compound AA | | 14.49 |
| cocoamidodimethyl propylsultaine | | 4.68 |
| sodium tridecylether (4.2) sulfate | | 4.96 |
| cocoimidazoline | | 4.37 |
| dye | | 0.002 |
| preservative | | 1.10 |
| fragrance | | 0.20 |
| deionized water | q.s to | 100 |

The resulting composition is a clear stable gel composition suitable for use as a concentrate shampoo or body cleanser with a viscosity of about 8000 cps as measured by a Brookfield Viscometer. The composition exhibits good spreadability and good cleansing characteristics.

When the above composition is tested for ocular irritation in accordance with the previously described modified Draize test, it is found to be a slight irritant.

EXAMPLE II

Additional compositions containing the same ingredients as in EXAMPLE I are prepared and the final pH in each is adjusted for various values in the range of pH 7.0 to pH 8.1 The resulting compositions are then evaluated for yield point and cold temperature (freeze/thaw cycle) stability.

The yield points in dynes/cm$^2$ are measured by a Rotoviscometer. The yield point of a composition is that point at which the composition becomes liquified or flowable and spreads easily as a result of an applied stress. The higher the yield point of a composition, the more difficult it is to spread and therefore the less desirable said composition is as a personal care or hair care product. The cold temperature or freeze-thaw cycle stability is a subjective evaluation of whether a composition retains its integrity and stability when subjected to varying temperatures. The compositions to be tested are subjected to temperatures sufficient to result in freezing for an overnight period and then permitted to melt at ambient room temperature and are then observed and graded as to their stability.

The results obtained are as follows:

| Composition pH | Yield Point dynes/cm | Freeze-Thaw |
|---|---|---|
| 7.0 | — | unstable |
| 7.2 | 9,870 | stable |
| 7.3 | 11,045 | stable |
| 7.4 | 10,340 | stable |
| 7.5 | 10,105 | stable |
| 7.6 | 11,750 | stable |
| 8.1 | 16,450 | stable |

The results indicated that a pH range of from about 7.2 to about 8.1 is required for the compositions of the present invention. At the pH less than 7.2 the freeze-thaw characteristics of the compositions are unsatisfactory and a pH greater than 8.1 the yield point values would indicate that the spreadability of the compositions would be unsatisfactory and the compositions would also tend to be more irritating at higher pH values.

EXAMPLE III

A gel detergent composition is prepared consisting of the following ingredients:

| Ingredient | wt/wt % |
| --- | --- |
| lauricmyristic amido 3-hydroxypropyl phosphobetaine | 5.00 |
| cocoimidazoline | 5.00 |
| sodium lauryl ether (3.0) sulfate | 10.00 |
| Compound BB | 10.00 |
| preservative | 0.05 |
| dye, fragrance | 0.25 |
| deionized water | q.s. to 100 |

The pH is adjusted to 7.7 with HCl.

This composition exhibits good spreadability characteristics and good cleansing properties.

EXAMPLE IV

A gel detergent composition is prepared consisting of the following ingredients:

| Ingredient | wt/wt % |
| --- | --- |
| cocoamido betaine | 5.00 |
| cocoamido disodium 3-hydroxypropyl phosphobetaine | 3.00 |
| $C_{14}$-$C_{16}$ olefin sulfonate | 5.00 |
| Compound CC | 20.00 |
| dye, fragrance | 0.25 |
| Dowicil 200 | 0.05 |
| deionized water | q.s. to 110 |

The pH is adjusted to 7.7 with dilute HCl.

This composition exhibits good spreadability characteristics and good cleansing properties.

EXAMPLE V

A gel detergent composition is prepared consisting of the following ingredients:

| Ingredient | wt/wt % |
| --- | --- |
| lauricimidazoline | 5.00 |
| sodium tridecyl (3) ether sulfate | 5.00 |
| Compound EE | 10.00 |
| Dowicil 200 | 0.05 |
| dye, fragrance | 0.25 |
| deionized water | q.s. to 100 |

The pH is adjusted to 7.5 with HCl.

This composition exhibits good spreadability characteristics and good cleansing properties.

EXAMPLE VI

A gel detergent composition is prepared consisting of the following ingredients:

| Ingredient | wt/wt % |
| --- | --- |
| lauricmyristic amido disodium 3-hydroxypropyl phosphobetaine | 2.50 |
| sodium tridecyl (3) ether sulfate | 2.50 |
| Compound FF | 5.00 |
| Dowicil 200 | 0.05 |
| dye, fragrance | 0.25 |
| deionized water | q.s. to 100 |

The pH is adjusted to 7.2 with dilute HCl.

This composition exhibits good spreadability characteristics and good cleansing properties.

EXAMPLE VII

A gel detergent composition is prepared consisting of the following ingredients:

| Ingredient | wt/wt % |
| --- | --- |
| cocoamido dimethylpropyl sultaine | 5.00 |
| cocoimidazoline | 5.00 |
| sodium tridecylether (4.2) sulfate | 5.00 |
| Compound DD | 25.00 |
| Dowicil 200 | 0.05 |
| dye, fragrance | 0.25 |
| deionized water | q.s. to 100 |

The pH is adjusted to 7.5 with citric acid.

When the above composition is tested for ocular irritation in accordance with the previously described modified Draize test, it is found to be a slight irritant.

The above composition and the composition of EXAMPLE I are tested for foam volume and stability in accordance with the previously described modified Ross-Miles test and yield the results shown in Table I below:

TABLE I

| | Foam Volume (mm) | % decay |
| --- | --- | --- |
| Composition of EXAMPLE I | 175 | 8.8 |
| Composition of Example II | 190 | 10.0 |

These results indicate that these compositions possess good foam volume and good foam stability.

EXAMPLE VIII

A gel detergent composition is prepared consisting of the following ingredients:

| Ingredient | wt/wt % |
| --- | --- |
| nonylphenoxy ether (4.0) sodium sulfate | 10.00 |
| Compound HH | 15.00 |
| lauric diethanolamide | 3.00 |
| Dowicil 200 | 0.05 |
| dye, fragrance | 0.25 |
| deionized water | q.s. to 100 |

The pH is adjusted to 7.3 with dilute $H_2SO_4$.

This composition exhibits good spreadability characteristics and good cleansing properties.

EXAMPLE IX

A gel detergent composition is prepared consisting of the following ingredients:

| Ingredient | wt/wt % |
| --- | --- |
| cocamidodimethylcarboxymethyl betaine | 7.0 |
| imidazoline | 3.0 |

| Ingredient | wt/wt % |
| --- | --- |
| sodium tridecyl ether (4.2) sulfate | 10.0 |
| Compound II | 40.0 |
| Dowicil 200 | 0.05 |
| dye, fragrance | 0.25 |
| deionized water | q.s. to 100 |

The pH is adjusted to 7.5 with dilute HCl.

This composition exhibits good spreadability characteristics and good cleansing properties.

EXAMPLE X

A gel detergent composition is prepared consisting of the following ingredients:

| Ingredient | wt/wt % |
| --- | --- |
| lauricmyristic amido propylmonosodium phosphitaine | 5.0 |
| sodium tridecyl ether (3.0) sulfate | 5.0 |
| Compound JJ | 15.0 |
| Dowicil 200 | 0.05 |
| dye, fragrance | 0.25 |
| deionized water | q.s. to 100 |

The pH is adjusted to 7.4 with dilute HCl.

This composition exhibits good spreadability characteristics and good cleansing properties.

EXAMPLE XI

A gel detergent composition is prepared consisting of the following ingredients:

| Ingredient | wt/wt % |
| --- | --- |
| lauricmyristic amido disodium 3-hydroxypropyl phosphobetaine | 15.0 |
| Compound LL | 5.0 |
| Dowicil 200 | 0.05 |
| dye, fragrance | 0.25 |
| deionized water | q.s. to 100 |

The pH is adjusted to 7.8 with dilute HCl.

This composition exhibits good spreadability characteristics and good cleansing properties.

EXAMPLE XII

A gel detergent composition is prepared consisting of the following ingredients:

| Ingredient | wt/wt % |
| --- | --- |
| sodium lauryl ether (4.0) sulfate | 10.0 |
| Compound KK | 10.0 |
| Dowicil 200 | 0.05 |
| dye, fragrance | 0.25 |
| deionized water | q.s to 100 |

The pH is adjusted to 7.5 with dilute HCl.

This composition exhibits good spreadability characteristics and good cleansing properties.

Various other features and embodiments of the present invention not specifically enumerated will be obvious to those skilled in the art, all of which may be achieved without departing from the spirit and the scope of the invention as defined by the following claims.

We claim:

1. A detergent composition wherein the active surfactant ingredients consist essentially of from about 1 to 30% by weight of the total composition of a modified rosin ester of the formula

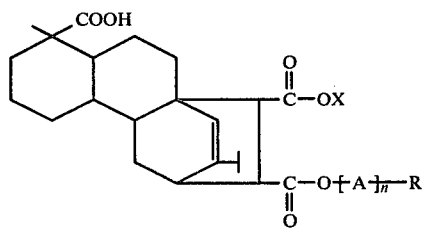

wherein R is hydrogen, alkyl containing from about 8 to 22 carbon atoms, hydroxyalkyl containing from about 8 to 22 carbon atoms, sorbitan monoesters of fatty acids containing from 8 to 22 carbon atoms or alkyl phenoxy containing from about 8 to 22 carbon atoms; X is hydrogen or an alkali metal salt; A is $CH_2$—$CH_2$—O or

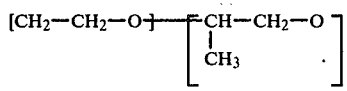

and n is an integer from 4; and from about 0.5 to 30.0% by weight of the total composition of at least one additional surfactant selected from the group consisting of anionic, nonionic, cationic and amphoteric surfactants with the proviso that the total amount of active surfactant ingredients should not be greater than about 40% by weight of the total composition and the proviso that the total amount of anionic and amphoteric surfactants should not be greater than about 20% by weight of the total composition.

2. The composition of claim 1 containing from about 2 to 10% by weight of the total composition of an anionic surfactant selected from the group consisting of alkylsulfate, alkylether sulfate, alkylmonoglyceryl ether sulfonate, alkylmonoglyceride sulfate, alkylmonoglyceride sulfonate, alkyl sulfonate, alkylaryl sulfonate, alkyl sulfosuccinate, alkyl sarcosinate, acyl isothionate, alkyl methyl tauride, fatty acid protein condensate and an alcohol ether carboxylate.

3. The composition of claim 1 containing from about 1 to 30% by weight of the total composition of a nonionic surfactant selected from the group consisting of alkylene oxide ethers of phenols, fatty alcohols, and alkyl mercaptans; alkylene oxide esters of fatty acid amides and condensation products of ethylene oxide with partial fatty acid esters.

4. The composition of claim 1 containing from about 0.5 to 3% of weight of the total composition of a cationic surfactant selected from the group consisting of mono- and bis-quaternary ammonium halides, tertiary amine salts, cationic polymers and triesters of phosphoric acid.

5. The composition of claim 1 containing from about 2 to 10% by weight of the total composition of an amphoteric surfactant selected from the group consisting of betaines, sultaines, n-alkylaminopropionates, n-alkylimino-dipropionates, phosphobetaines, phosphitaines, and imidazolines.

6. The composition of claim 1 having a pH range of from about 7.2 to 8.1.

7. The composition of claim 1 wherein the modified rosin ester is of the formula
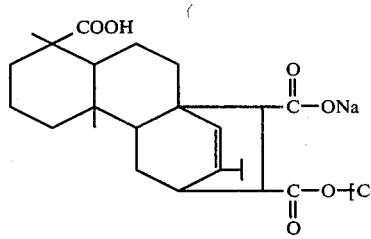
wherein R is sorbitan monopalmitate.
8. The composition of claim 1 wherein the modified rosin ester is of the formula
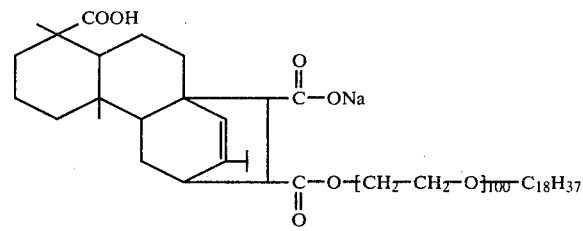
9. The composition of claim 1 wherein the modified rosin ester is of the formula
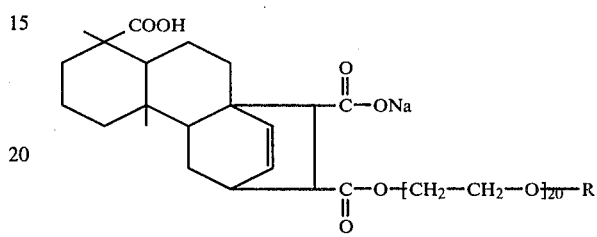
wherein R is sorbitan monococoate.